United States Patent
Kojima et al.

(10) Patent No.: US 11,152,559 B2
(45) Date of Patent: Oct. 19, 2021

(54) PIEZOELECTRIC ELEMENT, ULTRASONIC SENSOR, DISCHARGING HEAD, ULTRASONIC DEVICE, LIQUID DISCHARGING DEVICE, AND METHOD OF MANUFACTURING PIEZOELECTRIC ELEMENT

(71) Applicant: Seiko Epson Corporation, Tokyo (JP)

(72) Inventors: Chikara Kojima, Matsumoto (JP); Koji Ohashi, Matsumoto (JP)

(73) Assignee: Seiko Epson Corporation

( * ) Notice: Subject to any disclaimer, the term of this patent is extended or adjusted under 35 U.S.C. 154(b) by 718 days.

(21) Appl. No.: 15/926,213

(22) Filed: Mar. 20, 2018

(65) Prior Publication Data

US 2018/0277734 A1 Sep. 27, 2018

(30) Foreign Application Priority Data

Mar. 21, 2017 (JP) .............................. JP2017-054066

(51) Int. Cl.
  *H01L 41/047* (2006.01)
  *H01L 41/053* (2006.01)
  (Continued)

(52) U.S. Cl.
  CPC .......... *H01L 41/042* (2013.01); *A61B 8/4483* (2013.01); *B06B 1/0622* (2013.01); *B41J 2/14233* (2013.01); *H01L 27/20* (2013.01); *H01L 41/047* (2013.01); *H01L 41/053* (2013.01); *H01L 41/0805* (2013.01);
  (Continued)

(58) Field of Classification Search
  CPC . H01L 41/047; H01L 41/053; H01L 41/0805; H01L 41/0973
  See application file for complete search history.

(56) References Cited

U.S. PATENT DOCUMENTS

| 2006/0044359 A1 | 3/2006 | Sugahara |
| 2008/0062230 A1 | 3/2008 | Nozu et al. |

(Continued)

FOREIGN PATENT DOCUMENTS

| JP | H-09-327911 A | 12/1997 |
| JP | 2005-051688 A | 2/2005 |

(Continued)

OTHER PUBLICATIONS

Extended European Search Report for Application No. EP 18 16 2530 dated Dec. 6, 2018 (13 pages).

(Continued)

*Primary Examiner* — Derek J Rosenau
(74) *Attorney, Agent, or Firm* — Harness, Dickey & Pierce, P.L.C.

(57) ABSTRACT

A supporting film is provided on an opening and a wall of a substrate. A piezoelectric film is provided on a first region of the supporting film corresponding to the opening and a second region of the supporting film corresponding to the wall. The thickness of the piezoelectric film at the second region is smaller than that of the piezoelectric film provided at the first region. Therefore, vibration of the piezoelectric film in the first region is large, and vibration of the piezoelectric film in the second region is small. This alleviates disadvantages such as a loss of the vibration characteristics of a piezoelectric element.

8 Claims, 14 Drawing Sheets

(51) Int. Cl.

| | | |
|---|---|---|
| H01L 41/04 | (2006.01) | |
| H02N 2/00 | (2006.01) | |
| H01L 41/08 | (2006.01) | |
| H01L 41/113 | (2006.01) | |
| H01L 27/20 | (2006.01) | |
| B06B 1/06 | (2006.01) | |
| H01L 41/09 | (2006.01) | |
| H01L 41/318 | (2013.01) | |
| B41J 2/14 | (2006.01) | |
| H01L 41/332 | (2013.01) | |
| A61B 8/00 | (2006.01) | |

(52) U.S. Cl.
CPC ...... *H01L 41/0973* (2013.01); *H01L 41/1132* (2013.01); *H01L 41/318* (2013.01); *H01L 41/332* (2013.01); *H02N 2/001* (2013.01); *B41J 2002/14241* (2013.01); *B41J 2002/14419* (2013.01)

(56) References Cited

U.S. PATENT DOCUMENTS

| | | | |
|---|---|---|---|
| 2009/0244206 A1* | 10/2009 | Nakayama | B41J 2/1643 347/68 |
| 2009/0284568 A1 | 11/2009 | Yazaki | |
| 2011/0007114 A1* | 1/2011 | Nakayama | B41J 2/14233 347/68 |
| 2014/0296716 A1 | 10/2014 | Kiyose et al. | |
| 2015/0187347 A1 | 7/2015 | Kojima et al. | |
| 2017/0031024 A1 | 2/2017 | Kiyose et al. | |
| 2017/0128047 A1 | 5/2017 | Kiyose et al. | |

FOREIGN PATENT DOCUMENTS

| | | |
|---|---|---|
| JP | 2010-188694 A | 9/2010 |
| JP | 2014-195494 A | 10/2014 |
| JP | 2015-126449 A | 7/2015 |
| JP | 2016-005222 A | 1/2016 |
| JP | 2017-029270 A | 2/2017 |

OTHER PUBLICATIONS

Partial European Search Report for Application No. EP 18 16 2530 dated Sep. 4, 2018 (16 pages).

* cited by examiner

PIEZOELECTRIC ELEMENT, ULTRASONIC SENSOR, DISCHARGING HEAD, ULTRASONIC DEVICE, LIQUID DISCHARGING DEVICE, AND METHOD OF MANUFACTURING PIEZOELECTRIC ELEMENT

BACKGROUND

1. Technical Field

The present invention relates to a piezoelectric element, an ultrasonic sensor, a discharging head, an ultrasonic device, a liquid discharging device, and a method of manufacturing a piezoelectric element.

2. Related Art

A known ultrasonic element array includes a substrate having a first surface, in which a plurality of openings are formed, and a second surface opposite to the first surface, on which an insulating layer, a first electrode, a piezoelectric film and a second electrode are provided (see, for example, JP-A-2005-51688).

In JP-A-2005-51688, the area of each of the first electrodes and second electrodes is formed to be larger than that of the opening area of the opening. Edges of the first electrodes and second electrodes reach a wall provided between adjacent openings. The piezoelectric film has the same thickness between the first electrode and the second electrode, from a region overlapping with the opening to a region overlapping with the wall.

A region of the piezoelectric film on the openings of a side of the second surface is provided for vibration, and a region of the piezoelectric film on the wall is not provided for vibration.

In JP-A-2005-51688, the piezoelectric film has the same film thickness between the first electrode and the second electrode, which makes the piezoelectric film thickness in a region that is not provided for vibration the same as that in a region provided for vibration. Therefore, the piezoelectric film vibrates in the region that is not provided for vibration as well as the region that is provided for vibration. This results in the loss of vibration characteristics in the region that is not provided for vibration.

Furthermore, since the first electrode and the second electrode reach the region corresponding to the side of the second surface of the openings and even the wall provided between adjacent openings, unnecessary electric charges flow from the first and second electrodes into the piezoelectric film at the region that is not provided for vibration. The unnecessary electric charges cause the piezoelectric film in a non-vibration region to vibrate, which causes disadvantages such as film quality deterioration over time.

The disadvantage such as loss of vibration characteristics and deterioration of film thickness over time cannot be ignored in view of the tendency to miniaturize the structure and weakness of vibration output, of the piezoelectric element.

SUMMARY

An advantage of some aspects of the invention is to provide a piezoelectric element, an ultrasonic sensor, a discharging head, an ultrasonic device, a liquid discharging device, and a method of manufacturing a piezoelectric element capable of avoiding deterioration of film quality over time and loss of vibration characteristics.

A piezoelectric element according to an application example of the invention includes: a substrate having a plurality of openings penetrating therethrough and walls provided between the plurality of openings; a thin film provided on a first region closing the opening and a second region on the wall; and a piezoelectric film provided on the thin film on the first region and the second region, and a film thickness of the piezoelectric film provided on the thin film on the second region is smaller than that of the piezoelectric film provided on the thin film on the first region.

Here, the part of the piezoelectric film corresponding to the first region is provided for vibration, and the part of the piezoelectric film corresponding to the second region is not provided for vibration. The film thickness of the piezoelectric film provided on the thin film on the second region is smaller than that of the piezoelectric film provided on the thin film on the first region, and as a result, vibration in the region of the piezoelectric film that is provided for vibration is large, and vibration in the region of the piezoelectric film that is not provided for vibration is small. Since the vibration in the region that is provided for vibration is large, the piezoelectric element vibrates independently in each of the first regions adjacent to each other with the second regions interposed therebetween, whereby it is possible to mitigate the loss of vibration characteristics.

Furthermore, although electric charges flow in the piezoelectric film on the region that is not provided for vibration, since the film thickness of the region is smaller than that of the region that is provided for vibration, vibration in the part corresponding to the second region is smaller than vibration in the part corresponding to the first region, which leads to alleviation of the disadvantage such as deterioration of film quality due to change over time.

It is preferable that the piezoelectric element according to the application example further includes a first electrode provided between the piezoelectric film and the thin film, extending from the first region to the second region, and a second electrode provided on the piezoelectric film, and a part of the second electrode located in the second region does not overlap with the first electrode in a plan view from a thickness direction of the thin film.

In the application example with this configuration, when a voltage is applied to the piezoelectric film between the first electrode and the second electrode, the piezoelectric film vibrates. In the application example, since the part of the second electrode positioned on the second region does not overlap with the first electrode in the plan view from the thickness direction of the thin film, electric charges hardly flow in the part of the piezoelectric film corresponding to the second region.

Therefore, the vibration in the region of the piezoelectric film that is not provided for vibration is reduced, which leads to alleviation of the disadvantage such as deterioration of film quality due to change over time.

In the piezoelectric element according to the application example, it is preferable that the piezoelectric film on the second region includes a recess in which a region overlapping with the first electrode is a bottom of the recess in the plan view from the thickness direction of the thin film, and a total surface area of the bottom is larger than that of the first electrode on the second region.

In the application example with this configuration, the second electrode is provided in the vicinity of a tip opening of the recess of the piezoelectric film, and is not provided in the part corresponding to the recess. In addition, the area of the bottom of the recess is larger than that of the first electrode in the second region. In this way, even if a voltage is applied to the piezoelectric film between the first electrode and the second electrode on the second region, it is difficult for electric charges to flow in and around the recess.

Therefore, the vibration in the region of the piezoelectric film that is not provided for vibration is reduced, which leads to alleviation of the disadvantage such as deterioration of film quality due to change over time.

In the piezoelectric element according to the application example, it is preferable that the piezoelectric film on the first region vibrates the thin film on the first region when a voltage is applied, and the piezoelectric film on the second region suppresses vibration of the thin film on the second region when a voltage is applied.

In the application example with this configuration, the part corresponding to the first region and the part corresponding to the second region in the piezoelectric film are integrally formed. In this configuration, the first region of the thin film vibrates and the second region thereof does not vibrate, which results in suppression of the vibration of the first region.

Therefore, when a voltage is applied to the piezoelectric film, the vibration of the thin film of the first region is less likely to be transmitted to the second region, which leads to alleviation of the disadvantage such as deterioration of film quality due to change over time.

An ultrasonic sensor according to another application example of the invention includes a piezoelectric element, and a protective case that protects the piezoelectric element.

In this application example, the piezoelectric element is protected with the protective case. Therefore, the piezoelectric film is not directly exposed to the outside.

Here, just like the application example regarding the piezoelectric element, even if electric charges flow in the region of the piezoelectric film that is not provided for vibration, since the film thickness of the region is smaller than that of the region that is provided for vibration, the vibration of the part corresponding to the second region is smaller than the vibration of the part corresponding to the first region. Therefore, in the ultrasonic sensor, the vibration of the region of the piezoelectric film that is not provided for vibration is reduced, which leads to alleviation of the disadvantage such as deterioration of film quality due to change over time or the loss of vibration characteristics.

A discharging head according to another application example of the invention includes: a piezoelectric element, and a tank that is provided facing a thin film of the piezoelectric element, stores liquid therein, and includes a discharging port for discharging the liquid by driving the piezoelectric element in part thereof.

In this application example, since the discharging head is formed to include the piezoelectric element and the tank, the liquid stored in the tank is discharged from a discharging port by driving the piezoelectric element.

Here, just like the application example regarding the piezoelectric element, even if electric charges flow in the region of the piezoelectric film that is not provided for vibration, since the film thickness of the region is smaller than that of the region that is provided for vibration, the vibration of the part corresponding to the second region is smaller than the vibration of the part corresponding to the first region. Therefore, in the discharging head, the vibration of the region of the piezoelectric film that is not provided for vibration is smaller, which leads to alleviation of the disadvantage such as deterioration of film quality due to change over time or the loss of vibration characteristics.

An ultrasonic device according to another application example of the invention includes: an ultrasonic sensor, and a controller that controls the ultrasonic sensor.

In this application example, since the ultrasonic device is formed to include the ultrasonic sensor and the controller, the ultrasonic sensor is controlled by the controller.

Here, just like the application example regarding the piezoelectric element, even if electric charges flow in the region of the piezoelectric film that is not provided for vibration, since the film thickness of the region is smaller than that of the region that is provided for vibration, the vibration of the part corresponding to the second region is smaller than the vibration of the part corresponding to the first region. Therefore, in the ultrasonic device, the vibration of the region of the piezoelectric film that is not provided for vibration is smaller, which leads to alleviation of the disadvantage such as deterioration of film quality due to change over time or the loss of vibration characteristics.

A liquid discharging device according to another application example of the invention includes: a discharging head, and a controller that controls the discharging head.

In this application example, since the liquid discharging device is formed to include the discharging head and the controller, it is possible to accurately discharge liquid by controlling the discharging head by the controller.

Here, just like the application example regarding the piezoelectric element, even if electric charges flow in the region of the piezoelectric film that is not provided for vibration, since the film thickness of the region is smaller than that of the region that is provided for vibration, the vibration of the part corresponding to the second region is smaller than the vibration of the part corresponding to the first region. Therefore, in the liquid discharging device, the vibration of the region of the piezoelectric film that is not provided for vibration is smaller, which leads to alleviation of the disadvantage such as deterioration of film quality due to change over time or the loss of vibration characteristics.

A method of manufacturing a piezoelectric element according to an application example of the invention includes: forming a thin film having a first region and a second region on a substrate; forming a first electrode on one side of the thin film opposite to the side on which the substrate is provided, the first electrode extending from the first region to the second region; forming a piezoelectric film on the first electrode; forming a second electrode to be provided on the piezoelectric film; processing the piezoelectric film so that a thickness of the piezoelectric film on the second region is smaller than that of the piezoelectric film on the first region; and forming an opening in a part of the substrate corresponding to first region and forming a wall in a part corresponding to the second region.

In this application example, the forming of the thin film is performed to form the thin film having the first region and the second region on the substrate. As will be described later, the first region corresponds to the opening of the substrate, the second region corresponds to the wall partitioning the openings, and the first and second regions are formed alternately with each other. In the forming of the thin film, the location and dimensions of the first and second regions are set in advance depending on the dimensions of the opening and the walls of the piezoelectric element to be manufactured.

Then, the forming of the first electrode is performed to form the first electrode on the thin film, the forming of the piezoelectric film is performed to form the piezoelectric film on the first electrode, and the forming of the second electrode is performed to form the second electrode on the piezoelectric film. In this application example, processing of the piezoelectric film is further performed to make the thickness of the piezoelectric film on the second region smaller than that of the piezoelectric film on the first region. In the processing of the piezoelectric film, any desired technique can be used including, for example changing the thickness of the piezoelectric film by etching the second electrode. Then, the forming of the openings is performed to form the openings and the walls in a part on an opposite side of the part where the thin film of the substrate is formed. The openings are formed at the parts corresponding to the first region and the walls are formed at the parts corresponding to the second region. Therefore, the first region is provided for vibration, and the second region is not provided for vibration.

Therefore, through the processing of the piezoelectric film for making the thickness of the piezoelectric film on the second region smaller than that of the piezoelectric film on the first region, the piezoelectric element can be manufactured in which the disadvantage such as deterioration of film quality due to change over time or the loss of vibration characteristics is alleviated.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

First Embodiment

Hereinafter, an ultrasonic device according to a first embodiment will be described with reference to drawings.

Figure 1:
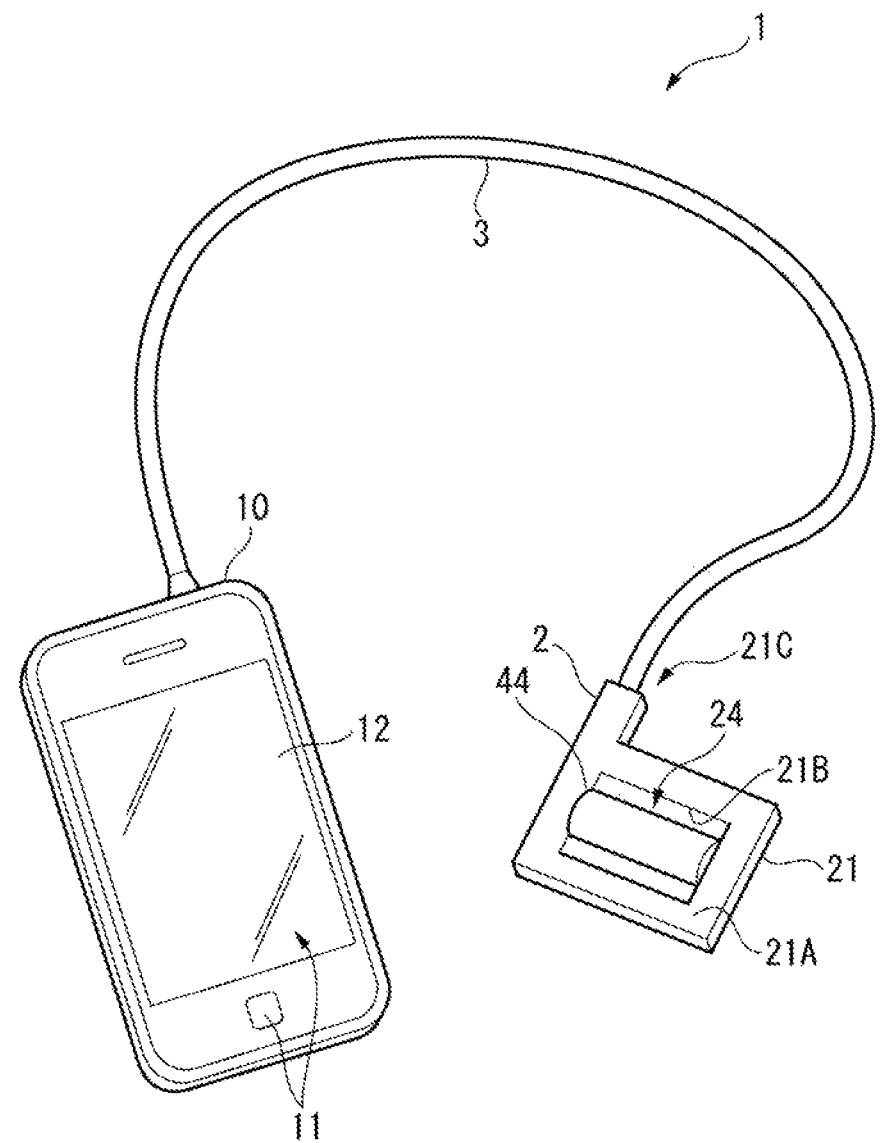
FIG. 1 is a perspective view illustrating a schematic configuration of an ultrasonic device of a first embodiment of the invention.

FIG. 1 is a perspective view illustrating a schematic configuration of the ultrasonic apparatus 1.

In FIG. 1, the ultrasonic apparatus 1 includes an ultrasonic probe 2 and a control device 10 electrically connected to the ultrasonic probe 2 through a cable 3.

The ultrasonic probe 2 in the ultrasonic apparatus 1 comes into contact with a living body (for example, human body), and waves from the ultrasonic probe 2 ultrasonic are transmitted into the living body. Further, the ultrasonic wave that is reflected by an organ in the living body is received by the ultrasonic probe 2, and based on the received signal, for example, an internal tomographic image of an area in the living body is acquired, and the state of the organ in the living body (for example, blood flow) is measured.

Configuration of Control Device

The control device 10 corresponds to a controller, and includes an operation unit 11 including a button, a touch panel, or the like, and a display 12. Although not shown, the control device 10 also includes a storage unit configured by a memory or the like, and a calculation unit configured by a Central Processing Unit (CPU) or the like. The control device 10 causes the calculation unit to execute various kinds of programs stored in the storage unit, to control the ultrasonic apparatus 1. For example, the control device 10 outputs a command for controlling the driving of the ultrasonic probe 2, displays an image of the internal structure of the living body formed based on received signals input from the ultrasonic probe 2 on the display 12, and displays the measured biometric data such as blood flow on the display 12. Examples of the control device 10 can include a tablet PC, a smartphone, a personal computer, and other terminal devices, and the manipulation of the ultrasonic probe 2 may be performed using a dedicate terminal.

Configuration of Ultrasonic Probe

Figure 2:
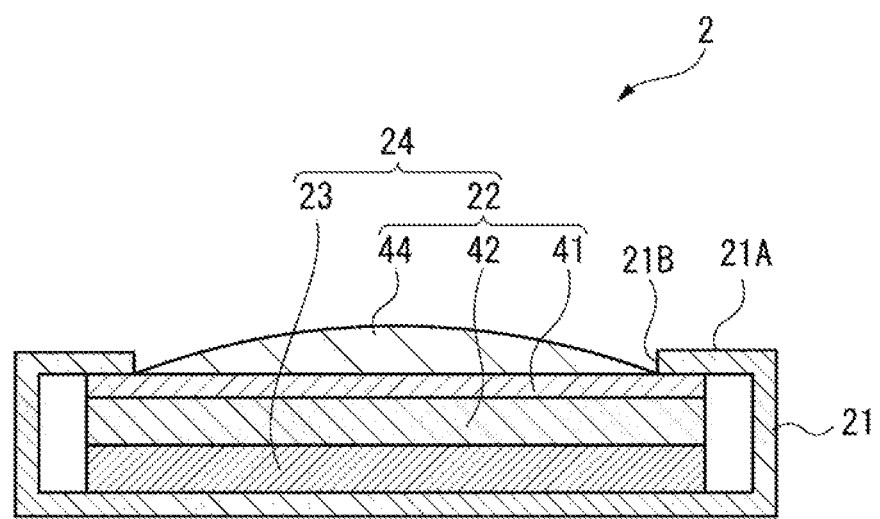
FIG. 2 is a cross sectional view illustrating the schematic configuration of the ultrasonic probe of the first embodiment of the invention.

FIG. 2 is a cross sectional view illustrating the schematic configuration of the ultrasonic probe 2.

In FIG. 2, the ultrasonic probe 2 includes a housing 21, an ultrasonic device 22 housed in the housing 21, and a circuit board 23 provided with a driver circuit for controlling the ultrasonic device 22 and the like. The ultrasonic device 22 and the circuit board 23 constitute an ultrasonic sensor 24.

Configuration of Housing

As shown in FIG. 1, the housing 21 is formed, for example, in a rectangular box shape in a plan view, and allows some of the ultrasonic device 22 to be exposed by forming a surface (sensor surface 21A) orthogonal to the thickness direction with a sensor window 21B. In addition, a passage hole 21C of a cable 3 is provided on a part of the housing 21 (a side in FIG. 1). The cable 3 is connected with the circuit board 23 in the housing 21 through the passage hole 21C. The gap between the cable 3 and the passage hole 21C is filled with, for example, a resin material to ensure waterproofness.

In the first embodiment, the ultrasonic probe 2 and the control device 10 are configured to be connected to each other using the cable 3, but the configuration is not limited thereto. For example, the ultrasonic probe 2 and the control device 10 may be connected to each other by wireless communication, or various configurations of the control device 10 may be provided in the ultrasonic probe 2.

Configuration of Circuit Board

The circuit board 23 is electrically connected to a signal terminal and a common terminal of the ultrasonic device 22, which will be described below, and controls the ultrasonic device 22 under the control of the control device 10.

Specifically, the circuit board 23 includes a transmission circuit, a reception circuit, and the like. The transmission circuit outputs a driving signal for ultrasonic transmission to the ultrasonic device 22. The reception circuit acquires a signal (received signal) output from the ultrasonic device 22 which has received the ultrasonic wave, performs amplification processing of the received signal, a A/D conversion processing, a phasing addition processing, or the like on the acquired signal, and outputs the signal to the control device 10.

Configuration of Ultrasonic Device

As shown in FIG. 2, the ultrasonic device 22 includes an element substrate 41, a sealing plate 42 as a protective case, an acoustic layer (not shown) and an acoustic lens 44.

Figure 3:
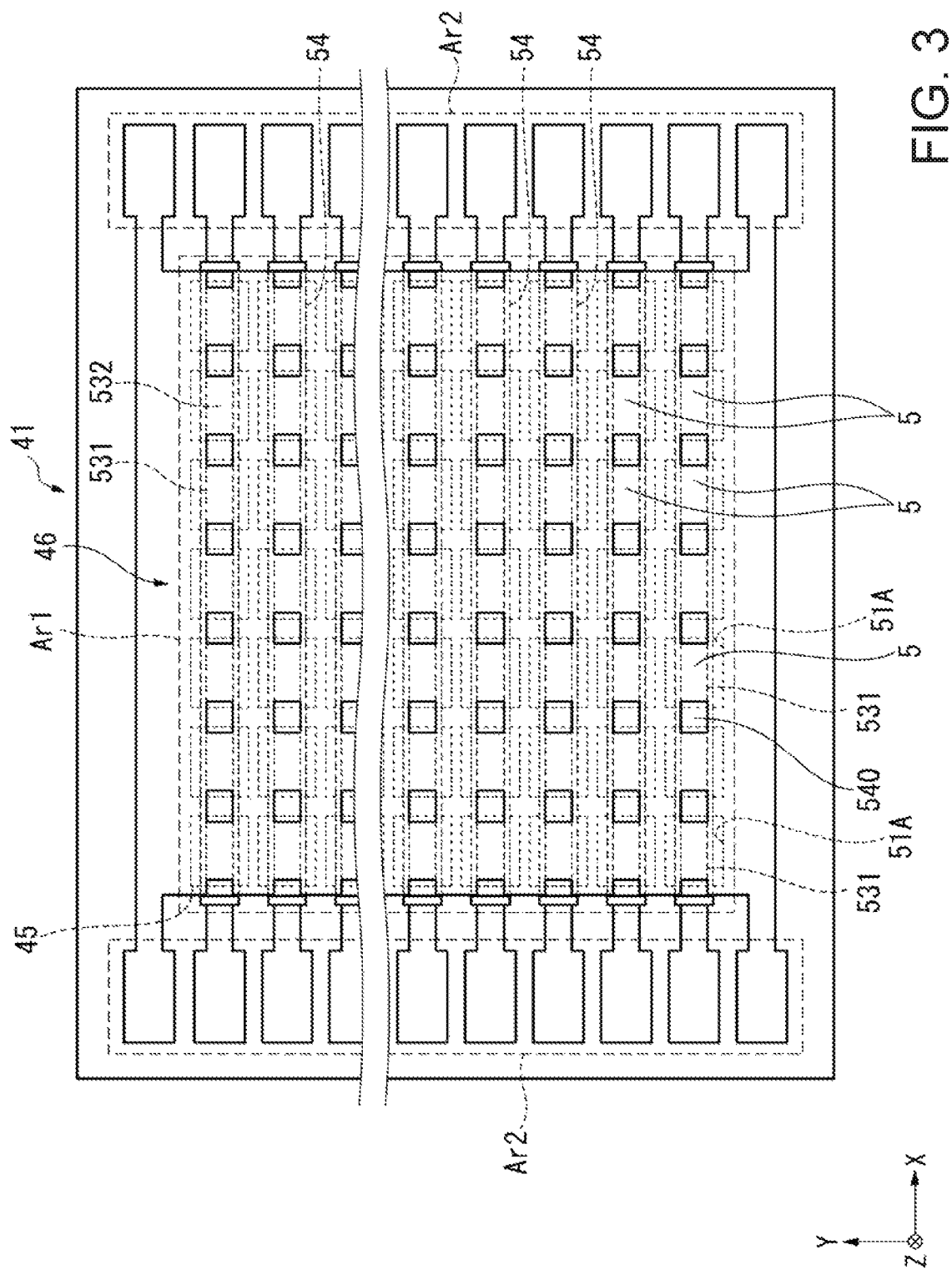
FIG. 3 is a plan view illustrating an element substrate in the ultrasonic device of the first embodiment of the invention.
Figure 4:
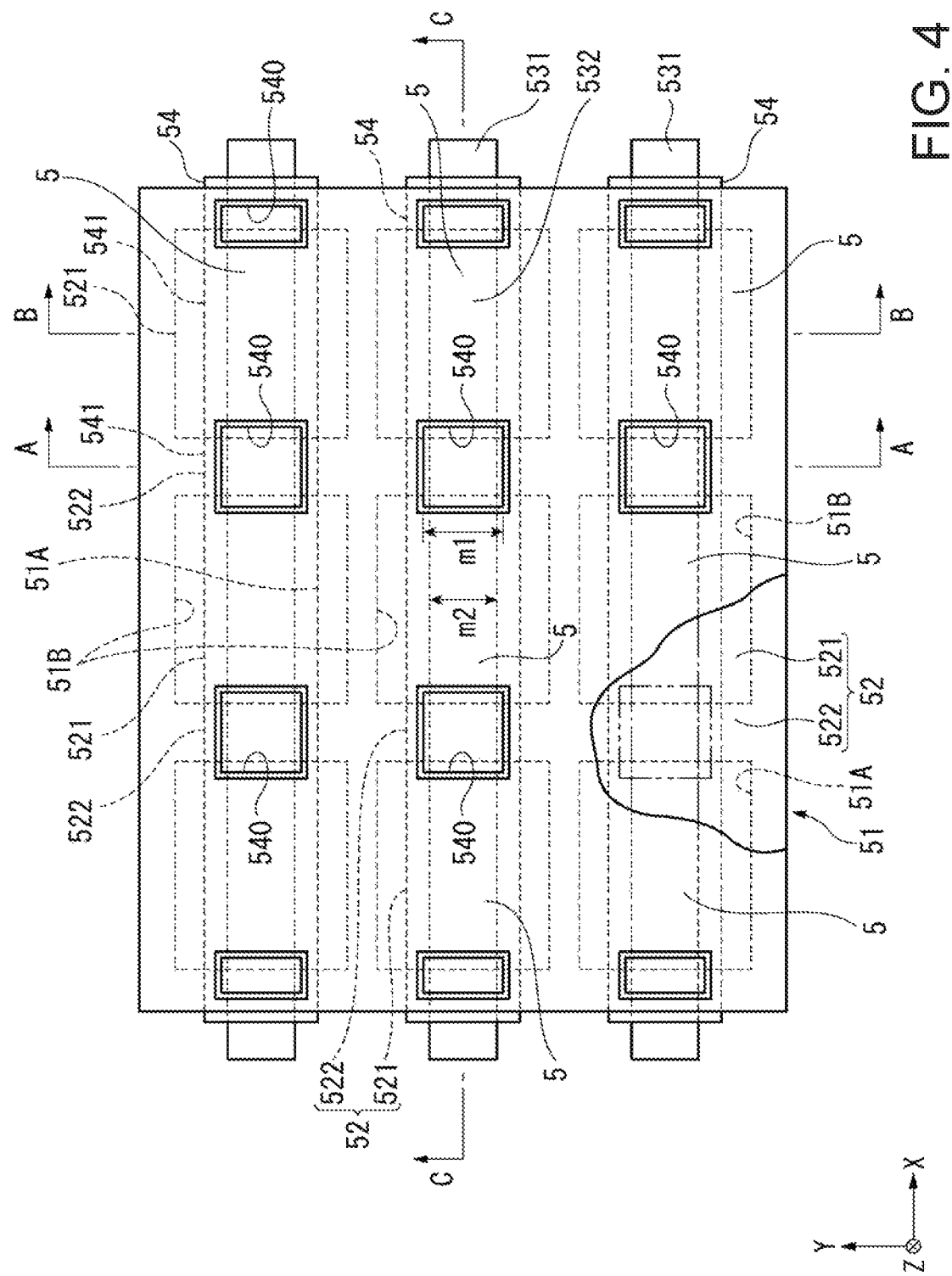
FIG. 4 is an enlarged plan view illustrating a part of the element substrate.
Figure 5:
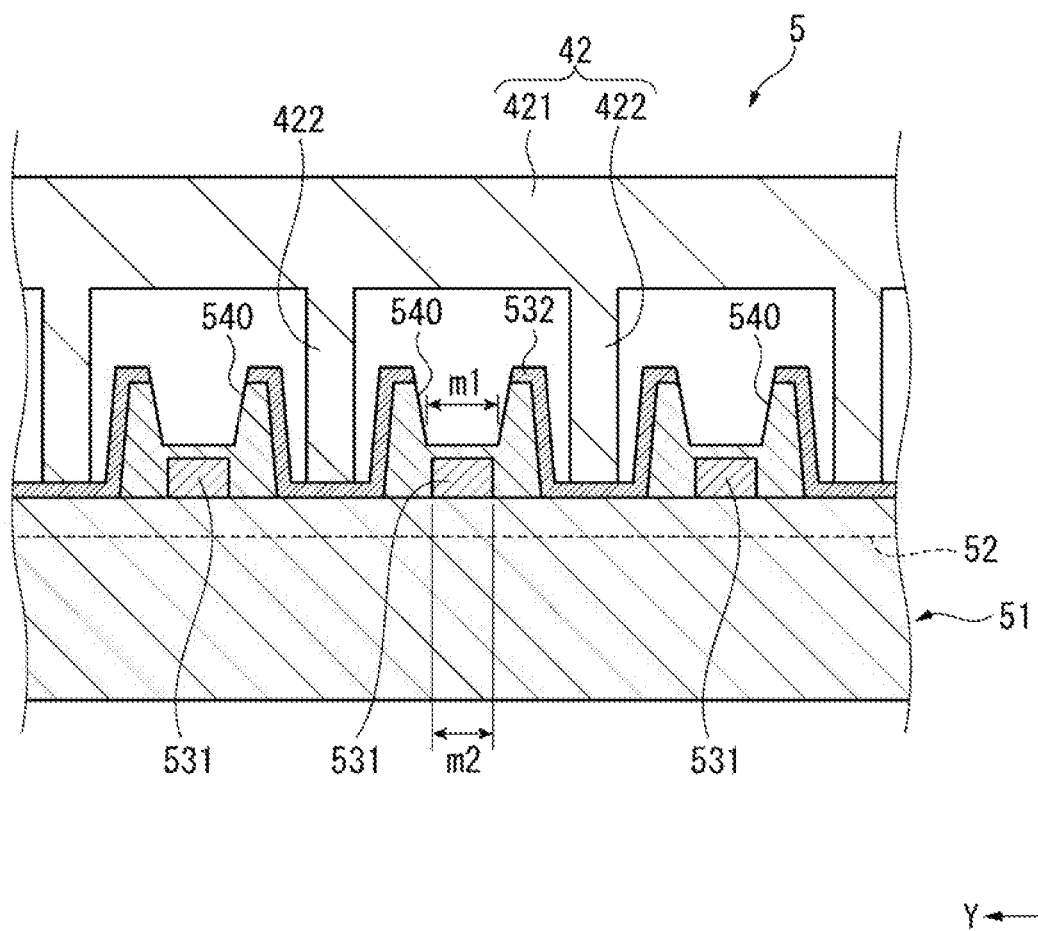
FIG. 5 is a cross sectional view taken along the line A-A in FIG. 4.
Figure 6:
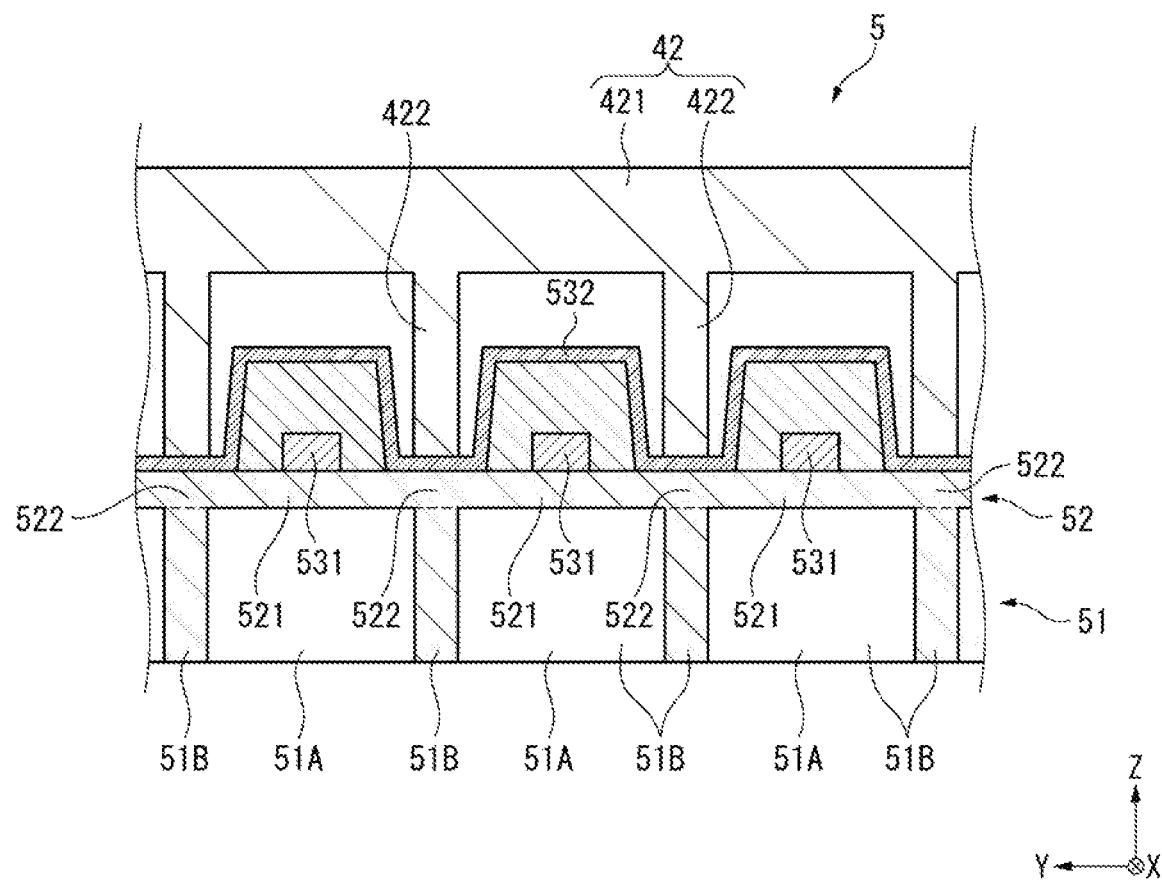
FIG. 6 is a cross sectional view taken along the line B-B in FIG. 4.
Figure 7:
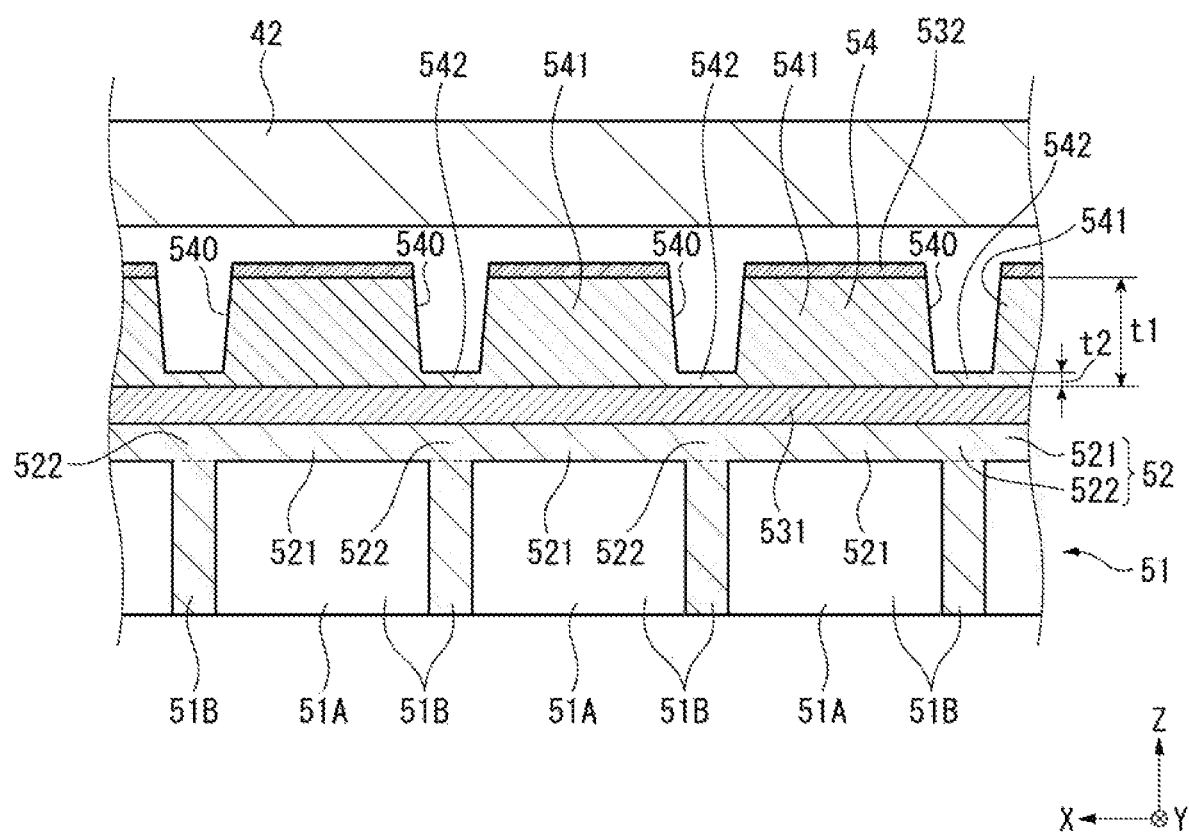
FIG. 7 is a cross sectional view taken along the line C-C in FIG. 4.

FIG. 3 is a view schematically illustrating the element substrate 41 that constitutes the ultrasonic device 22 when viewed from the sealing plate 42 side. FIG. 4 is an enlarged view of FIG. 3. FIG. 5 is a schematic cross sectional view of the ultrasonic device 22 taken along the line A-A in FIG. 4, FIG. 6 is a schematic cross sectional view of the ultrasonic device 22 taken along the line B-B in FIG. 4, and FIG. 7 is a schematic cross sectional view of the ultrasonic device 22 taken along the line C-C in FIG. 4.

Configuration of Element Substrate

In FIG. 3, in a plan view of the element substrate 41 seen from a substrate thickness direction (Z direction) (hereinafter, also simply referred to as "plan view"), in the central array region Ar1 of the element substrate 41, an ultrasonic transducer array 46 including ultrasonic transducers 45 for transmitting and receiving ultrasonic waves is provided. The ultrasonic transducer array 46 is implemented as a one-dimensional array where a plurality of ultrasonic transducers 45 is disposed in a matrix. That is, the ultrasonic transducer array 46 has a plurality of transmission/reception columns, each functioning as a transmission/reception channel of 1CH. Along the Y direction (a slice direction), a plurality of ultrasonic transducers 45 are disposed, which constitutes one transmission/reception column, and along the X direction (a scan direction) the transmission/reception column is arranged in plural. In FIG. 3, for ease of description, a reduced number of ultrasonic transducers 45 are illustrated, but actually more ultrasonic transducers 45 are disposed therein.

On the element substrate 41, a plurality of piezoelectric elements 5 is disposed in a lattice pattern along the X direction and the Y direction.

Configuration of Piezoelectric Element

The specific configuration of the piezoelectric element 5 is shown in FIGS. 4 to 7.

In FIGS. 4 to 7, the piezoelectric element 5 is configured to include the substrate 51, a supporting film 52 (thin film) provided on the substrate 51, an lower electrode 531 provided on the supporting film 52 as the first electrode, a piezoelectric film 54 provided on the lower electrode 531, and an upper electrode 532 provided on the piezoelectric film 54 as the second electrode.

The substrate 51 supports the supporting film 52, and has a plurality of openings 51A penetrating therethrough and walls 51B provided between the openings 51A. The substrate 51 is formed of a semiconductor substrate such as Si, for example. The openings 51A correspond to ultrasonic transducers 45, respectively (see FIG. 3). On the front side of the opening 51A an acoustic lens (which is not shown in FIG. 5 to FIG. 7) is disposed, and inside the opening 51A there is formed an acoustic layer.

The supporting film 52 is made of, for example, $SiO_2$, or a laminate of $SiO_2$ and $ZrO_2$, or the like, and is provided on the entire back side of the substrate 51. The thickness dimension of the supporting film 52 is significantly smaller compared to the thickness dimension of the substrate 51.

The supporting film 52 has the first region 521 closing the back side of each opening 51A, and the second region 522 provided on (aligned with) each wall 51B. The first region 521 and the second region 522 are continuously formed corresponding to the arrangement of the opening 51A and the wall 51B.

The piezoelectric film 54 is formed, for example, using a transition metal oxide having a perovskite structure, specifically, lead zirconate titanate (PZT) containing Pb, Ti and Zr.

Along the X direction, a plurality of rows of piezoelectric films 54 is arranged.

In FIG. 7, the piezoelectric film 54 is provided on the first region 521 and the second region 522 of the supporting film 52 extending along the X direction. Here, the part 541 of the piezoelectric film 54 corresponding to (provided on) the first region 521 is provided for vibration, and the part 542 corresponding to (provided on) the second region 522 is not provided for vibration.

The part 541 corresponding to the first region 521 and the part 542 corresponding to the second region 522 in the piezoelectric film 54 are integrally formed. In the piezoelectric film 54, the part 541 corresponding to the first region 521 vibrates the first region 521 when a voltage is applied, and the part 542 corresponding to the second region 522 suppresses vibration of the first region 521 when a voltage is applied.

The part 541 of the piezoelectric film 54 corresponding to the first region 521 has a different film thickness than the part 542 of the piezoelectric film 54 corresponding to the second region 522, which are adjacent to each other in the X direction. The film thickness of the part 541 of the piezoelectric film 54 corresponding to the first region 521 is t1, and the film thickness of the part 542 of the piezoelectric film 54 corresponding to the second region 522 is t2, and the film thickness t2 is smaller than that of t1. The t1 and t2 is desirably set, for example, so that the film thickness t1 is 1050 nm, and the film thickness t2 is less than 1050 nm and more than 200 nm.

As materials of the lower electrode 531 and the upper electrode 532, for example, a metal material such as Pt, Ir, Ti, Zr, Au, Ni, NiCr, TiW, Al, Cu or the like can be used.

The lower electrode 531 is provided between the piezoelectric film 54 and the supporting film 52 and along the piezoelectric film 54.

The upper electrode 532 is disposed so as to cover the area where the piezoelectric film 54 is disposed, excluding some parts of the area of the piezoelectric film 54, and is disposed on the second region 522 of the supporting film 52 in the area where the piezoelectric film 54 is not disposed (see FIG. 5 to FIG. 7).

As shown in FIG. 4, FIG. 5 and FIG. 7, in the plan view from the thickness direction of the supporting film 52, the piezoelectric film 54 corresponding to the second region 522 has a rectangular planar shaped recess 540, in which the region overlapping with the lower electrode 531 is the bottom. The recess 540 is not provided with the upper electrode 532. That is, in the plan view from the thickness direction of the supporting film 52 the part of the upper electrode 532 positioned on the second region 522 does not overlap with the lower electrode 531 (see FIG. 5 and FIG. 7).

The dimension m1 of the bottom of the recess 540 in the Y direction is larger than the dimension m2 of the lower electrode 531 in the Y direction (see FIG., 4 and FIG. 5), and the dimension of the bottom of the recess 540 in the X direction is the same as that of the dimension of the lower electrode 531 overlapping with the bottom of the recess 540 in the plan view. In this way, the area (total surface area) of the bottom of the recess 540 where the upper electrode 532 is not provided is larger than that of the lower electrode 531 on the second region 522.

In the ultrasonic transducer 45, a pulse wave voltage of a predetermined frequency applied between the lower electrode 531 and the upper electrode 532 causes the first region 521 of the supporting film 52 corresponding to the opening 51A to vibrate and accordingly transmit ultrasonic waves. When the first region 521 of the supporting film 52 is vibrated by the ultrasonic waves reflected from an object, a voltage is generated above and below the piezoelectric film 54. Accordingly, by detecting the voltage generated between the lower electrode 531 and the upper electrode 532, the ultrasonic waves are detected, that is, received.

Configuration of Sealing Plate

The sealing plate 42 has a planar shape in the plan view from the thickness direction, for example, the same shape as that of the element substrate 41, and is formed of a semiconductor substrate such as Si or an insulating substrate. Since the material and thickness of the sealing plate 42 affect the frequency characteristics of the ultrasonic transducer 45, the material and thickness may be set based on the center frequency of ultrasonic waves which are transmitted and received by the ultrasonic transducer 45.

The sealing plate 42 is provided with a connection portion for connecting each terminal to the circuit board 23 at a position facing a terminal region Ar2 of the element substrate 41. The connection portion, for example, has a configuration including an opening provided in the element substrate 41 and a wiring member such as a flexible printed circuit (FPC), a cable, a wire and the like for connecting the respective terminals and the circuit board 23 to each other through the opening.

The sealing plate 42 has a plate 421 covering the upper electrode 532 and a sealing plate foot 422 provided on the plate 421 and joined to the adjacent piezoelectric element (see FIG. 5 and FIG. 6). In addition to the effect as a protective case for protecting the piezoelectric element 5, the sealing plate 42 also has the effect of suppressing vibration leakage to the adjacent piezoelectric element 5 by joining the sealing plate foot 422 between the piezoelectric elements 5.

Configuration of Acoustic Lens

In FIG. 1 and FIG. 2, the acoustic lens 44 is disposed on the front surface of the element substrate 41. The acoustic lens 44 is brought into close contact with the surface of the living body and allows the ultrasonic waves transmitted from the ultrasonic transducer 45 to converge in the living body. In addition, the acoustic lens 44 propagates the ultrasonic waves reflected in the living body to the ultrasonic transducer 45 through the acoustic layer.

Method of Manufacturing Piezoelectric Element

Figure 8:
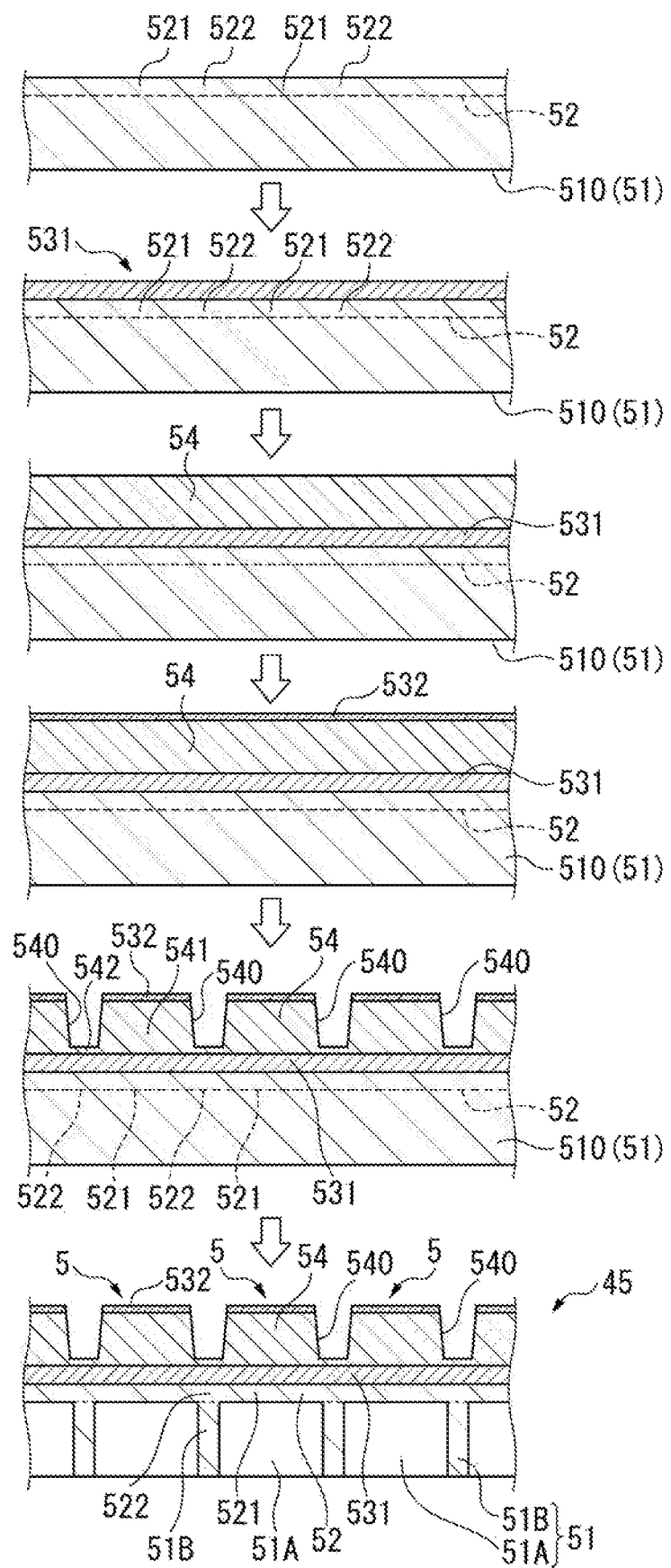
FIG. 8 is a schematic view illustrating a method of manufacturing a piezoelectric element.

Next, a method of manufacturing the ultrasonic transducer 45 having a plurality of piezoelectric elements 5 based on FIG. 8. FIG. 8 is a view schematically illustrating each of steps in the method of manufacturing the ultrasonic transducer 45.

First, as shown at the first from the top in FIG. 8, a thin film forming step of forming the supporting film 52 on the substrate is executed.

Therefore, on one surface of a substrate 510 made of a silicon wafer, a thermal oxidation treatment is performed to form a film of $SiO_2$, and a $ZrO_2$ film for preventing lead diffusion is formed by sputtering to form the supporting film 52. In the supporting film 52, the first region 521 and the second region 522 are set according to the dimensions of the openings 51A and the walls 51B of the piezoelectric elements 5 to be manufactured.

Next, as shown at the second from the top in FIG. 8, a first electrode forming step is executed.

Therefore, an electrode material is formed on the supporting film 52 by sputtering and then subjected to etching treatment to form the lower electrode 531 as the first electrode along the X direction.

As shown at the third from the top in FIG. 8, a piezoelectric film forming step of forming the piezoelectric film 54 on the lower electrode 531 is executed.

Therefore, lead titanate zirconate (PZT) is formed on the lower electrode 531 and the supporting film 52 by, for example, a melting method. In the formation of lead titanate zirconate (PZT) by a solution method, a PZT solution is applied the supporting film 52 and the lower electrode 531 (application step). Then, the applied PZT solution is fired (firing step). In the firing step, for example, pre-baking is performed at 400° C., and RTA firing is performed at 700° C. The application step and the firing step are repeated a plurality of times, whereby the piezoelectric film 54 having a desired thickness dimension is formed.

As shown at the fourth from the top in FIG. 8, a second electrode forming step of forming the upper electrode 532 as the second electrode on the piezoelectric film 54 is executed.

Therefore, the upper electrode 532 is formed on the piezoelectric film 54 by sputtering.

As shown at the fifth from the top in FIG. 8, a piezoelectric film processing step is executed.

Therefore, the portion of the piezoelectric film 54 and the upper electrode 532 corresponding to the second region 522 of the supporting film 52 is subjected to etching treatment to form the recess 540, and the film thickness t2 of the part 542 of piezoelectric film 54 corresponding to the second region 522 is smaller than the film thickness t1 of the part 541 of the piezoelectric film 54 corresponding to the first region 521. The etching treatment is executed including the upper electrode 532.

As shown at the sixth from the top in FIG. 8, an opening forming step is executed.

Therefore, etching treatment is executed on the side of the substrate 510 opposite to the side on which the supporting film 52 is formed, and the opening 51A is formed in the part corresponding to the first region 521. Since the part of the substrate 510 corresponding to the second region 522 is not subjected to etching treatment, the part remains as the wall 51B.

As described above, the ultrasonic transducer 45 is manufactured.

Relationship Between Transmission Sensitivity and Piezoelectric Residual Film

The relationship between the transmission sensitivity and a piezoelectric residual film will be described with reference to FIG. 9.

Figure 9:
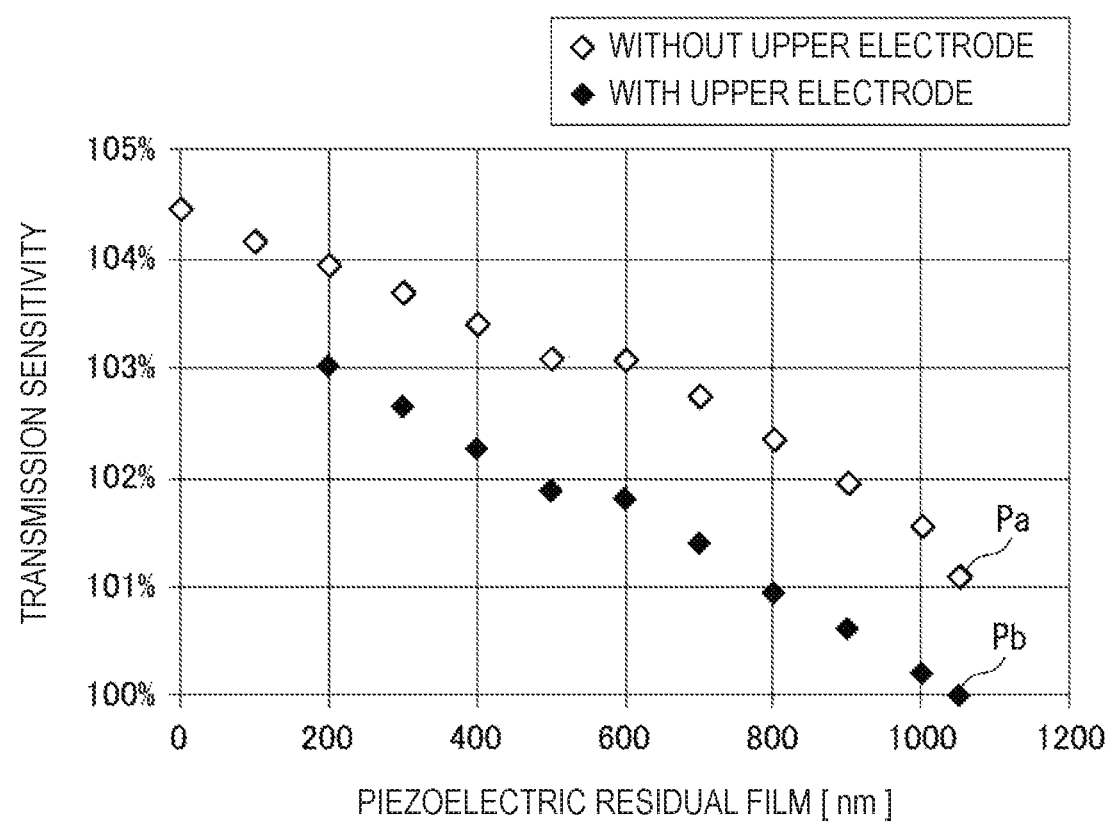
FIG. 9 is a graph illustrating a relationship between transmission sensitivity and thickness of piezoelectric residual film.

In the graph of FIG. 9, the piezoelectric residual film means the film thickness t2 of the part 542 of the piezoelectric film 54 corresponding to the second region 522 (see FIG. 7). The transmission sensitivity is indicated as an output value when a predetermined voltage is applied between the lower electrode 531 and the upper electrode 532. FIG. 9 shows a set of output values for both the presence and absence of the upper electrode 532 as a ratio of the change in the piezoelectric residual film (film thickness t2) when the transmission sensitivity Pb in the film thickness t2 of 1050 nm is set to 100%, where the film thickness (1050 nm) is the same as the film thickness t1 of the part 541 corresponding to the first region 521.

In FIG. 9, regardless of presence or absence of the upper electrode 532 on the part 542 of the piezoelectric film 54 corresponding to the second region 522, as the piezoelectric residual film (film thickness t2) is smaller, in other words, as the depth of the recess 540 increases, the transmission sensitivity increases. Furthermore, although the film thickness of the piezoelectric film 54 is the same between the first region 521 and the second region 522, the transmission sensitivity Pa without the upper electrode 532 is higher than the transmission sensitivity Pb when the upper electrode 532 is present. Regardless of the film thickness t2 of the piezoelectric residual film, that is, the part 542 of the piezoelectric film 54 corresponding to the second region 522, the transmission sensitivity becomes high when there is no upper electrode 532 on the part 542 corresponding to the second region 522.

Relationship Between Reception Sensitivity and Piezoelectric Residual Film

The relationship between the reception sensitivity and the piezoelectric residual film will be described with reference to FIG. 10.

Figure 10:
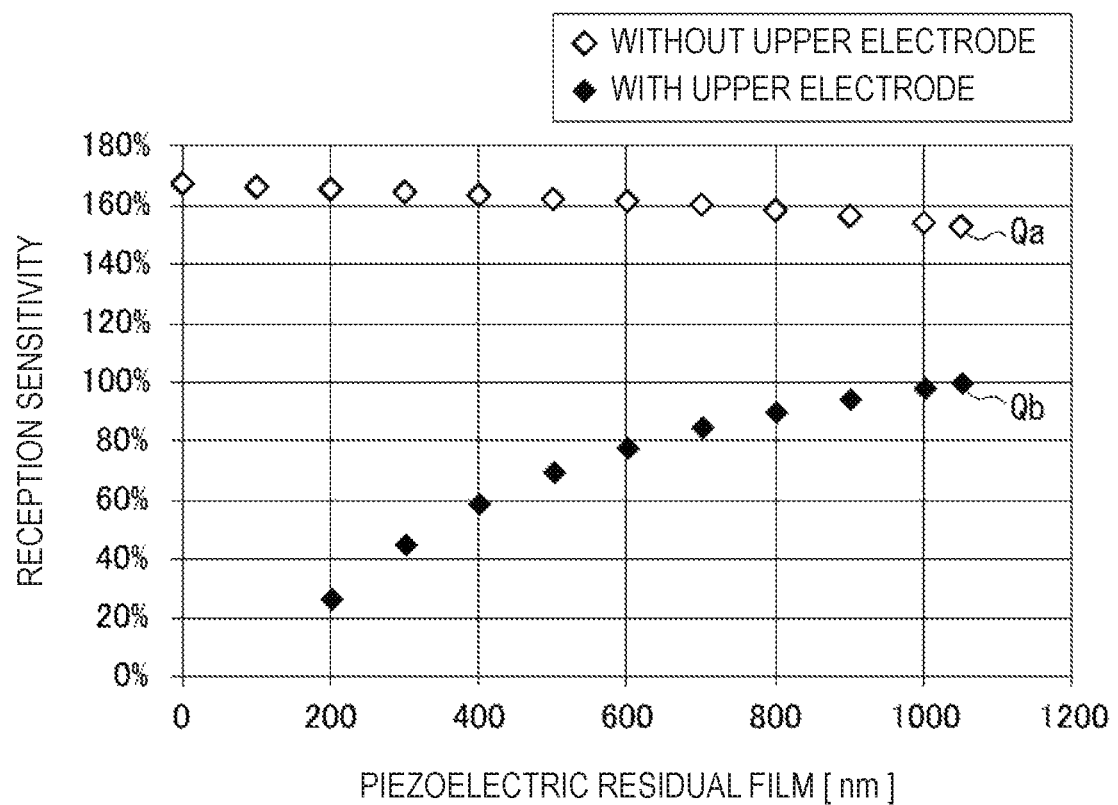
FIG. 10 is a graph illustrating a relationship between reception sensitivity and thickness of piezoelectric residual film.

In the graph of FIG. 10, the reception sensitivity means the voltage applied between the lower electrode 531 and the upper electrode 532 when the ultrasonic wave is received. Therefore, FIG. 10 shows a set of output values for both the presence and absence of the upper electrode 532 as a ratio of the change in the piezoelectric residual film (film thickness t2) when the reception sensitivity Qb in the film thickness t2 of 1050 nm is set to 100%, where the film thickness (1050 nm) is the same as the film thickness t1 of the part 541 corresponding to the first region 521.

In FIG. 10, although the film thickness of the piezoelectric film 54 is the same between the first region 521 and the second region 522, the reception sensitivity Qa without the upper electrode 532 is higher than the reception sensitivity Qb when the upper electrode 532 is present. In addition, regardless of the size of the piezoelectric residual film, the reception sensitivity becomes high when there is no upper electrode 532 on the part 542 corresponding to the second region 522. Furthermore, when there is no upper electrode 532 on the part 542 of the piezoelectric film 54 corresponding to the second region 522, as the piezoelectric residual film (film thickness t2) becomes small, the reception sensitivity becomes high.

Effect of First Embodiment

In the first embodiment, the supporting film 52 is provided on the opening 51A and the wall 51B in the substrate 51, and the piezoelectric film 54 is provided on the first region 521 of the supporting film 52 corresponding to the opening 51A and the second region 522 of the supporting film 52 corresponding to the wall 51B. Here, the film thickness t1 of the piezoelectric film 54 provided on the second region 522 is smaller than the film thickness t2 of the piezoelectric film 54 provided on the first region 521. Therefore, in the piezoelectric film 54, vibration of the region that is provided for vibration is increased, and vibration of the region that is not provided for vibration is reduced, which leads to alleviation of the disadvantage such as deterioration of film quality due to change over time or the loss of vibration characteristics of the piezoelectric element 5. That is, As understood from the graphs in FIG. 9 and FIG. 10, the film thickness t1 of the piezoelectric film 54 provided on the second region 522 is smaller than the film thickness t2 of the piezoelectric film 54 provided on the first region 521, whereby the transmission sensitivity and the reception sensitivity are improved. Furthermore, since vibration in the region that is not provided for vibration is small, it is possible to alleviate the disadvantage such as deterioration of film quality due to change over time.

The part of the upper electrode 532 positioned on the second region 522 does not overlap with the lower electrode 531. That is, when the upper electrode 532 is not on the part 542 of the piezoelectric film 54 corresponding to the second region 522, vibration in the region of the piezoelectric film 54 that is not provided for vibration becomes smaller, which leads to alleviation of the disadvantage such as deterioration of film quality due to change over time or the loss of vibration characteristics. That is, as shown in the graphs in FIG. 9 and FIG. 10, the transmission sensitivity and the reception sensitivity are improved.

The piezoelectric film 54 on the second region 522 has the recess 540 in which the region overlapping with the lower electrode 531 is the bottom, and the area of the bottom is larger than that of the lower electrode 531 on the second region 522. Therefore, although a voltage is applied to the piezoelectric film 54 between the upper electrode 532 and the lower electrode 531 on the second region 522, electric charges do not easily flow around the recess 540 and vibration in the region of the piezoelectric film 54 that is not provided for vibration is reduced, which leads to alleviation of the disadvantage such as deterioration of film quality due to change over time or the loss of vibration characteristics.

The part 541 corresponding to the first region 521 and the part 542 corresponding to the second region 522 in the piezoelectric film 54 are integrally formed. As a result, even if the supporting film 52 of the first region 521 vibrates, the supporting film 52 of the second region 522 does not vibrate, which results in suppression of the vibration of the first region. Therefore, the vibration of the first region 521 of the piezoelectric film 54 of the supporting film 52 is not easily transmitted to the second region 522, and accordingly vibration of the region of the piezoelectric film that is not provided for vibration is reduced, which leads to alleviation of the disadvantage such as deterioration of film quality due to change over time or the loss of vibration characteristics.

Since the ultrasonic sensor 24 is configured to include the piezoelectric element 5 and the sealing plate 42 as the protective case, the piezoelectric film 54 is directly exposed to the outside.

Second Embodiment

Hereinafter, a second embodiment of the invention will be described with reference to FIG. 11 and FIG. 12. In the second embodiment, a printer 100 will be described to include a piezoelectric element. In the description of the second embodiment, the same components as those of the first embodiment are denoted by the same reference numerals, and the description thereof will not be repeated.

Figure 11:
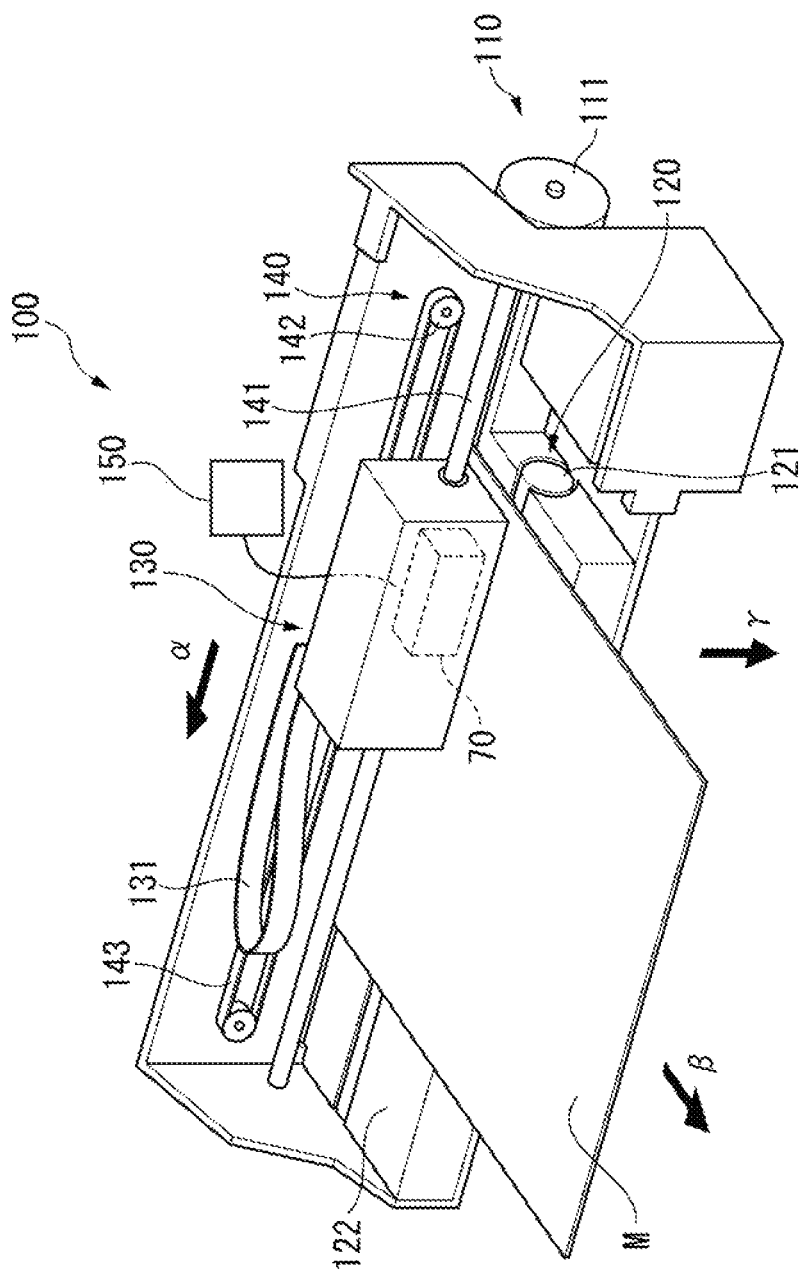
FIG. 11 is a view illustrating a schematic configuration of a printer of a second embodiment of the invention.
Figure 12:
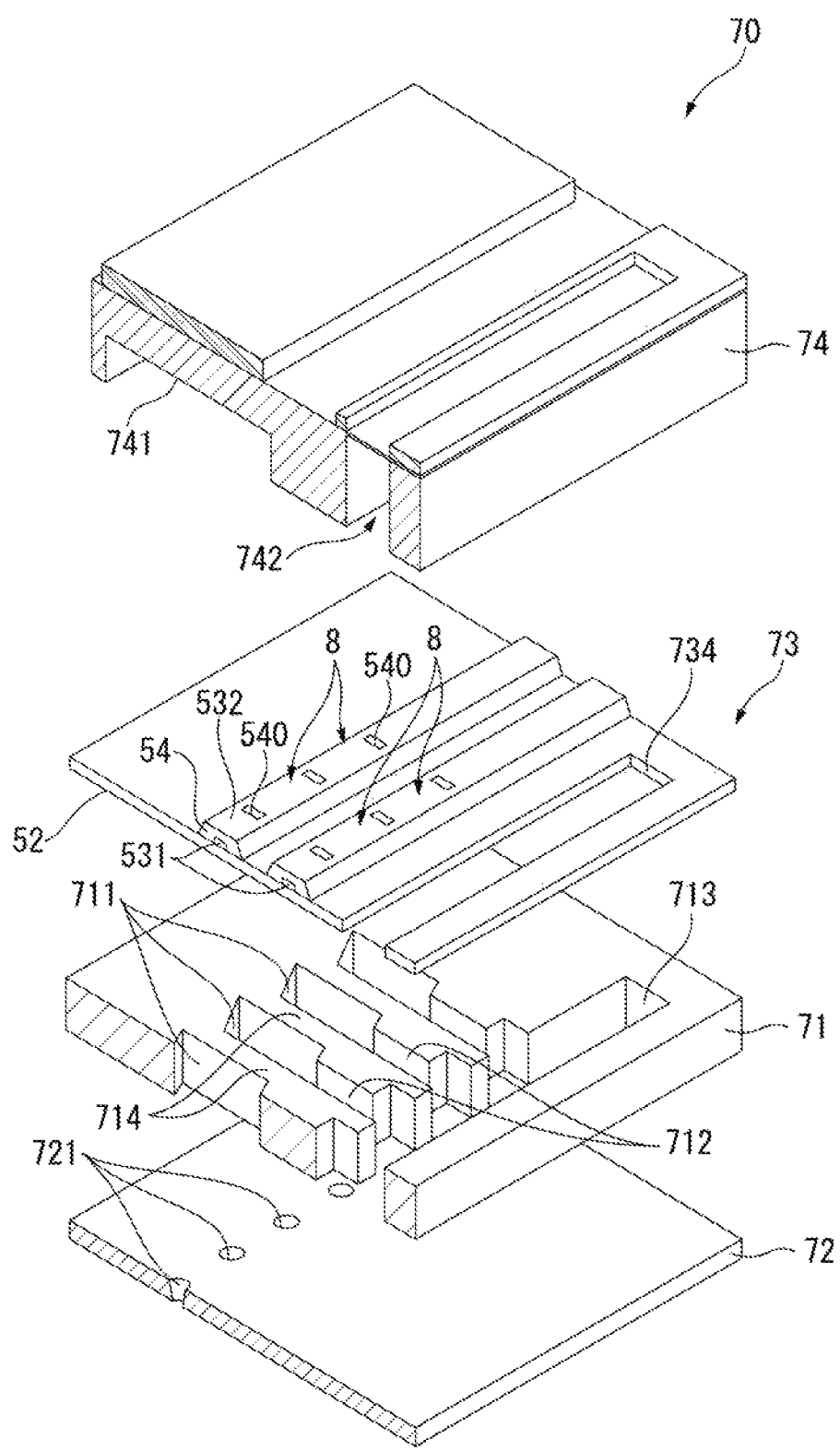
FIG. 12 is a schematic exploded perspective illustrating a recording head of the second embodiment of the invention.

FIG. 11 shows a configuration example of the appearance of the printer 100, and FIG. 12 schematically shows a recording head 70 of the printer 100.

In FIG. 11, the printer 100 corresponds to a liquid discharging device, and includes a supply unit 110 that supplies a media, a transport unit 120 that transports the media, a carriage 130 to which the recording head 70 is attached, a carriage moving unit 140 that moves the carriage 130, and a controller 150 that controls the printer 100. The printer 100 controls each of the units 110, 120 and 140 and the carriage 130 based on data input from an external apparatus such as a personal computer, and prints an image on the media M, for example.

The supply unit 110 supplies the media M to the position where the image is formed. For example, the supply unit 110 includes a roll body 111 on which the media M is wound, a roll drive motor (not shown), a roll drive wheel train (not shown), and the like. Based on a command from the controller 150, the roll drive motor is rotationally driven, and the rotational force of the roll drive motor is transmitted to a roll body 111 through the roll drive wheel train. In this way, the roll body 111 rotates, and a paper sheet that is wound around the roll body 111 is supplied to the downstream side (+β side) in the β direction (sub scanning direction).

The transport unit 120 transports the media M supplied from the supply unit 110 along the β direction. For example, the transport unit 120 includes a transport roller 121, a follower roller (not shown) that follows the transport roller 121 and is disposed with the medium M pinched between the transport roller 121 and the follower roller, and a platen 122 provided downstream of the transport roller 121 in the β direction. When the transport roller 121 receives a driving force transmitted from the transport motor (not shown) and the transport motor is driven under the control of the controller 150, the transport roller 121 is rotationally driven by the rotational force and the medium M is transported along the β direction in a state where the medium M is pinched between the transport roller 121 and the follower roller.

In the carriage 130, the recording head 70 and the like for printing an image on the medium M are attached. The recording head 70 and the like are connected to the controller 150 through a cable 131. The recording head 70 will be described later. The carriage 130 is provided so as to be movable by the carriage moving unit 140 along the α direction (main scanning direction) intersecting with the β direction.

The carriage moving unit 140 reciprocates the carriage 130 along the α direction. For example, the carriage moving unit 140 includes a carriage guide shaft 141, a carriage motor 142, a timing belt 143, and the like. The carriage guide shaft 141 is disposed along the α direction, and both ends are fixed to a housing of the printer 100. The carriage motor 142 drives the timing belt 143. The timing belt 143 is supported substantially in parallel with the carriage guide shaft 141, and a part of the carriage 130 is fixed. When the carriage motor 142 is driven based on a command from the controller 150, the timing belt 143 is driven in forward and reverse directions, and the carriage 130 fixed the timing belt 143 is guided by the carriage guide shaft 141 to reciprocate.

The recording head 70 ejects the ink supplied from an ink tank (not shown) in the γ direction intersecting with the α direction and the β direction to form the image on the medium M.

FIG. 12 shows the recording head 70.

In FIG. 12, the recording head 70 corresponds to a discharging head, and includes a pressure chamber forming substrate 71, a nozzle plate 72, an actuator unit 73, a sealing plate 74 as a protective case, and the like.

The pressure chamber forming substrate 71 is, for example, a plate material made of a silicon single crystal substrate or the like. In the pressure chamber forming substrate 71, a plurality of pressure chambers 711, ink supply paths 712 for supplying ink to the pressure chambers 711, and a communicating portion 713 communicating with the pressure chambers 711 through the ink supply paths 712 are formed. Here, the pressure chamber 711 corresponds to the opening portion in the second embodiment, and the pressure chamber 711 is partitioned by the wall 714.

The plurality of pressure chambers 711 are provided in one-to-one correspondence with respective nozzles 721 constituting a nozzle row formed on the nozzle plate 72 as described later. That is, each of the pressure chambers 711 is formed at the same pitch as a formation pitch of the nozzle 721 along the nozzle row direction.

The communicating portion 713 is formed along the plurality of the pressure chambers 711. The communicating portion 713 is a tank that communicates with a communicating opening portion 734 of a supporting film 52 and a liquid chamber empty portion 742 of the sealing plate 74, which will be described later, and is filled with ink supplied from an ink tank (not shown). The ink filled in the communicating portion 713 is supplied to the pressure chamber 711 through the ink supply path 712.

The ink supply path 712 is formed with a narrower width than the pressure chamber 711, and is a part that serves as a flow resistance to the ink flowing from the communicating portion 713 into the pressure chamber 711.

The nozzle plate 72, which is the component of a discharging port through which ink is discharged, has a nozzle row in which a plurality of nozzles 721 is arranged and is bonded to one surface of the pressure chamber forming substrate 71 (the surface opposite to the actuator unit 73). The plurality of nozzles 721 are formed at a pitch corresponding to the dot formation density (for example, 300 dpi). The nozzle plate 72 is made of, for example, glass ceramic, silicon single crystal substrate, stainless steel or the like.

The actuator unit 73 includes a supporting film 52 on a side of the pressure chamber forming substrate 71 opposite to the nozzle plate 72, and a lower electrode 531, a piezoelectric film 54 and a upper electrode 532 laminated on the supporting film 52, and a recess 540 is formed in a part corresponding to a second region (not shown in FIG. 12). In the second embodiment, the pressure chamber forming substrate 71 corresponds to the substrate on which openings and walls are formed, and the piezoelectric element 8 is configured by including the pressure chamber forming substrate 71, the supporting film 52, the lower electrode 531, the piezoelectric film 54, and the upper electrode 532.

As the supporting film 52, for example, silicon dioxide ($SiO_2$) having a thickness of 300 to 2000 nm is preferably used. As an insulator film (not shown) formed on the supporting film 52, for example, zirconium oxide ($ZrO_x$) having a thickness of 30 to 600 nm is preferably used.

The sealing plate 74 is bonded to the surface of the actuator unit 73 opposite to the pressure chamber forming substrate 71. On the surface of the sealing plate 74 on the actuator unit 73 side, a housing space 741 capable of housing the piezoelectric element 8 is formed.

In a region of the sealing plate 74 corresponding to the communicating opening portion 734 and the communicating portion 713, the liquid chamber empty portion 742 is provided. The liquid chamber empty portion 742 communicates with the communicating opening portion 734 and the communication portion 713, and forms a reservoir to be an ink chamber common to the pressure chambers 711. Although not shown, a wiring opening penetrating in the thickness direction is provided in the sealing plate 74 at a position corresponding to the terminal region of the actuator unit 73. The electrode terminals of the terminal region are exposed in the wiring opening. The electrode terminals are connected to a wiring member (not shown) connected to the printer main body.

In the recording head 70 having the above-mentioned configuration, the ink is taken in from the ink cartridge, and the flow path including the reservoir, the ink supply path 712, the pressure chamber 711, and the nozzle 721 is filled with the ink. When the respective piezoelectric elements 8 corresponding to the pressure chamber 711 are driven by the supply of the drive signal from the printer main body, the first region of the supporting film 52 corresponding to the pressure chamber 711 is displaced, and a pressure fluctuation occurs in the pressure chamber 711. By controlling the pressure fluctuation, ink is ejected from the nozzle 721.

In the piezoelectric element 8 in the second embodiment, the same effects as those in the first embodiment can be obtained.

MODIFICATION EXAMPLE

The invention is not limited to the embodiments described above, and modifications, improvements and structures obtained by appropriately combining embodiments within the scope capable of achieving an object of the invention are to be included in the invention.

Figure 13:
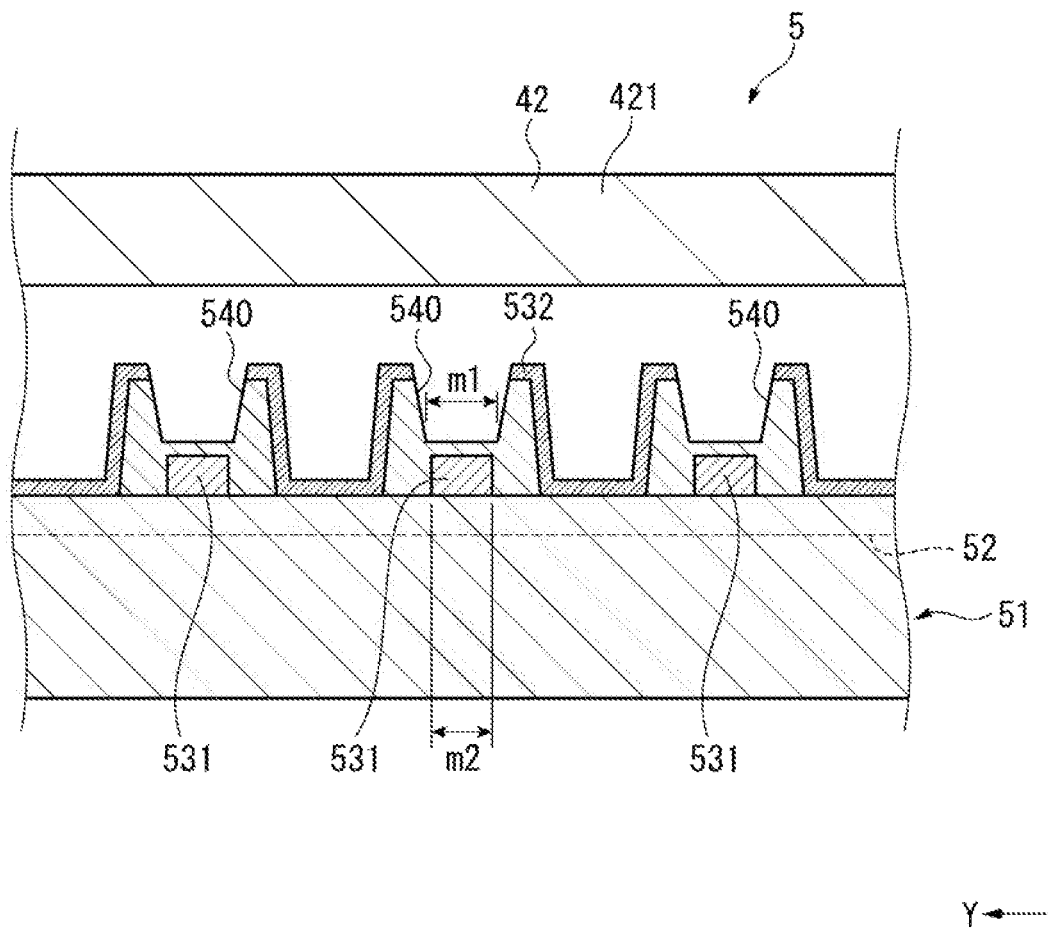
FIG. 13 is a view illustrating a modification example of the invention and corresponding to FIG. 5.
Figure 14:
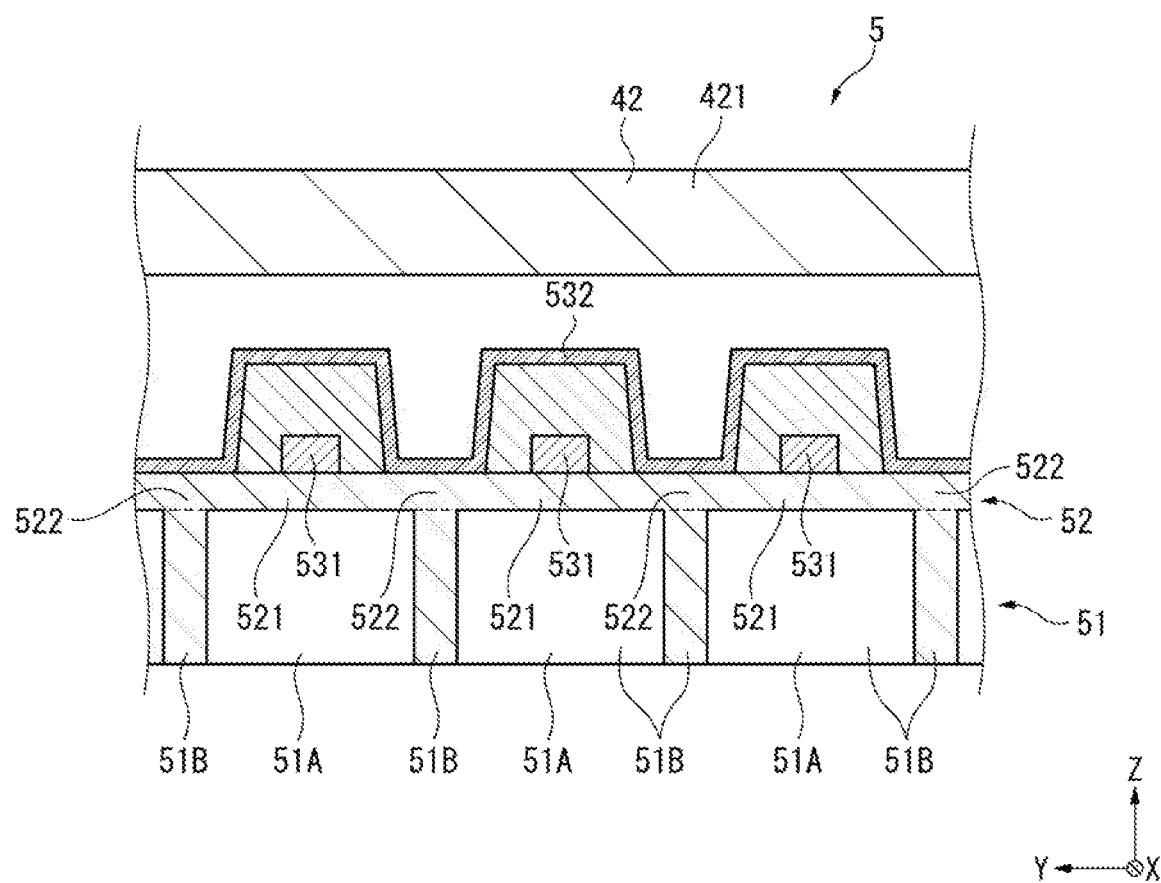
FIG. 14 is a view illustrating the modification example and corresponding to FIG. 6.

In the first embodiment, the sealing plate 42 is configured to include the plate 421 and the sealing plate foot 422. However, in the invention, as shown in FIG. 13 and FIG. 14, the sealing plate 42 may have a configuration without the sealing plate foot 422.

In the first embodiment, the planar shape of the recess 540 is rectangular. However, in the invention, other shapes such as circle and triangle may be used.

In each of the above embodiments, the lower electrode 531 and the upper electrode 532 are made of a metal material, but the invention is not limited thereto. For example, the lower electrode 531 and the upper electrode 532 may be made using a tin oxide-based conductive material such as indium tin oxide (ITO) or fluorine-doped tin oxide (FTO), a zinc oxide-based conductive material, strontium ruthenate ($SrRuO_3$), lanthanum nickelate ($LaNiO_3$), an element conductive dopant such as elemental doped strontium titanate, an electrically conductive polymer, or the like.

In the first embodiment, as an electronic apparatus, the ultrasonic device of which the measurement object is the organ in the living body has been described by way of example, the invention is not limited thereto. For example, it is possible to apply configurations of the embodiments described above and modification examples to a measuring machine that performs detection of defects or inspection of aging on various kinds of structures as measurement objects. Also, for example, when a semiconductor package, a wafer, or the like is the measurement object, the same applies to a measuring machine that performs detection of defects on the measurement object.

The entire disclosure of Japanese Patent Application No. 2017-054066 filed Mar. 21, 2017 is expressly incorporated by reference herein.

What is claimed is:

1. A piezoelectric element comprising:
   three axes orthogonal to each other being defined as an X-axis, a Y-axis, and a Z-axis;
   a substrate having a plurality of through openings therein and a plurality of walls separating each of the plurality of through openings, the substrate being plate-shaped and extending along the X-axis and the Y-axis, the substrate having a thickness along the Z-axis;
   a thin film provided on the substrate, the thin film being configured with first regions and second regions, each of the first regions spanning each of the plurality of through openings so that one end opening of each of the plurality of through openings is closed by the thin film, the second regions being aligned with the plurality of walls;
   a plurality of first electrodes disposed on the thin film, each of the plurality of first electrodes extending along the X-axis alternately on the first regions and the second regions of the thin film;
   a piezoelectric film provided on the plurality of first electrodes and the thin film located at positions corresponding to spaces between adjacent two first electrodes of the plurality of first electrodes;
   a second electrode disposed on the piezoelectric film except for a plurality of third regions of the piezoelectric film, the plurality of third regions overlapping with both the second regions of the thin film and the plurality of first electrodes along the Z-axis; and
   a plurality of recesses formed at the plurality of third regions of the piezoelectric film,
   wherein a first thickness of the piezoelectric film on the first regions of the thin film is larger than a second thickness of the piezoelectric film on the second regions of the thin film, and
   an area along the X-axis and the Y-axis of each of bottoms of the plurality of recesses is larger than an area along the X-axis and the Y-axis of each of the plurality of first electrodes aligned with the second regions of the thin film along the Z-axis.

2. The piezoelectric element according to claim 1, wherein the piezoelectric film on the first regions of the thin film is configured to vibrate the first regions of the thin film when a voltage is applied between the plurality of first electrodes and the second electrode, and the piezoelectric film on the second regions of the thin film is configured to suppress vibration of the second regions of the thin film when the voltage is applied between the plurality of first electrodes and the second electrode.

3. The piezoelectric element according to claim 1 further comprising a protective case housing the piezoelectric element.

4. The piezoelectric element according to claim 2 further comprising a protective case housing the piezoelectric element.

5. A discharging head comprising:
   a piezoelectric element including:
      three axes orthogonal to each other being defined as an X-axis, a Y-axis, and a Z-axis;
      a substrate having a plurality of through openings therein and a plurality of walls separating each of the plurality of through openings, the substrate being plate-shaped and extending along the X-axis and the Y-axis, the substrate having a thickness along the Z-axis;
      a thin film provided on the substrate, the thin film being configured with first regions and second regions, each of the first regions spanning each of the plurality of through openings so that one end opening of each of the plurality of through openings is closed by the thin film, the second regions being aligned with the plurality of walls;
      a plurality of first electrodes disposed on the thin film, each of the plurality of first electrodes extending along the X-axis alternately on the first regions and the second regions of the thin film;
      a piezoelectric film provided on the plurality of first electrodes and the thin film located at positions corresponding to spaces between adjacent two first electrodes of the plurality of first electrodes;

a second electrode disposed on the piezoelectric film except for a plurality of third regions of the piezoelectric film, the plurality of third regions overlapping with both the second regions of the thin film and the plurality of first electrodes along the Z-axis; and a plurality of recesses formed at the plurality of third regions of the piezoelectric film; and a tank that is provided facing the thin film of the piezoelectric element, the tank being configured to store liquid therein, the tank including a discharging port, the discharge port being configured to discharge the liquid by driving the piezoelectric element, wherein a first thickness of the piezoelectric film on the first regions of the thin film is larger than a second thickness of the piezoelectric film on the second regions of the thin film, and an area along the X-axis and the Y-axis of each of bottoms of the plurality of recesses is larger than an area along the X-axis and the Y-axis of each of the plurality of first electrodes aligned with the second regions of the thin film along the Z-axis.

6. The discharging head according to claim 5
wherein the piezoelectric film on the first regions of the thin film is configured to vibrate the first regions of the thin film when a voltage is applied between the plurality of first electrodes and the second electrode, and
the piezoelectric film on the second regions of the thin film is configured to suppress vibration of the second regions of the thin film when a voltage is applied between the plurality of first electrodes and the second electrode.

7. A piezoelectric element comprising:
three axes orthogonal to each other being defined as an X-axis, a Y-axis, and a Z-axis;
a substrate having a plurality of through openings therein and a plurality of walls separating each of the plurality of through openings, the substrate being plate-shaped and extending along the X-axis and the Y-axis, the substrate having a thickness along the Z-axis;
a film provided on the substrate, the film being configured with first regions and second regions, each of the first regions of the film spanning each of the plurality of through openings so that one end opening of each of the plurality of through openings is closed by the film, the second regions being aligned with the plurality of walls;

a plurality of first electrodes disposed on the film, each of the plurality of first electrodes extending along the X-axis alternately on the first regions and the second regions of the film;

a piezoelectric film provided on the plurality of first electrodes and the film located at positions corresponding to spaces between adjacent two first electrodes of the plurality of first electrodes, the piezoelectric film on the first regions of the film having a substantially constant first thickness, the piezoelectric film on the second regions of the film having a substantially constant second thickness;

a second electrode disposed on the piezoelectric film except for a plurality of third regions of the piezoelectric film, the plurality of third regions overlapping with both the second regions of the film and the plurality of first electrodes along the Z-axis; and a plurality of recesses formed at the plurality of third regions of the piezoelectric film, wherein the substantially constant first thickness of the piezoelectric film on the first regions of the film is larger than the substantially constant second thickness of the piezoelectric film on the second regions of the film, and an area along the X-axis and the Y-axis of each of bottoms of the plurality of recesses is larger than an area along the X-axis and the Y-axis of each of the plurality of first electrodes aligned with the second regions of the film along the Z-axis.

8. The piezoelectric element according to claim 7,
wherein the piezoelectric film on the first regions on the film is configured to vibrate the first regions of the film when a voltage is applied between the plurality of first electrodes and the second electrode, and
the piezoelectric film walls on the second regions of the film is configured to suppress vibration of the second regions of the film when the voltage is applied between the plurality of first electrodes and the second electrode.

* * * * *